(12) United States Patent
Dishner et al.

(10) Patent No.: US 11,213,290 B2
(45) Date of Patent: Jan. 4, 2022

(54) METHODS AND SYSTEMS FOR DOUBLE LOOP STITCHING

(71) Applicants: Preston Dishner, Piney Flats, TN (US); Lia Lynn Winter, Pittsburgh, PA (US)

(72) Inventors: Preston Dishner, Piney Flats, TN (US); Lia Lynn Winter, Pittsburgh, PA (US)

(73) Assignee: Winter Innovations, Inc., Knoxville, TN (US)

( * ) Notice: Subject to any disclaimer, the term of this patent is extended or adjusted under 35 U.S.C. 154(b) by 301 days.

(21) Appl. No.: 16/537,088

(22) Filed: Aug. 9, 2019

(65) Prior Publication Data

US 2019/0358023 A1 Nov. 28, 2019

Related U.S. Application Data

(63) Continuation-in-part of application No. 16/151,591, filed on Oct. 4, 2018, now Pat. No. 10,792,036.

(60) Provisional application No. 62/586,690, filed on Nov. 15, 2017.

(51) Int. Cl.
*A61B 17/06* (2006.01)

(52) U.S. Cl.
CPC .... *A61B 17/06* (2013.01); *A61B 2017/06057* (2013.01)

(58) Field of Classification Search
CPC .................. A61B 17/04; A61B 17/06; A61B 2017/06057; A61F 2/0811
See application file for complete search history.

(56) References Cited

U.S. PATENT DOCUMENTS

| 1,293,660 | A | 2/1919 | Armstrong |
| 1,591,021 | A | 7/1926 | Davis |
| 5,368,595 | A | 11/1994 | Lewis |
| 7,326,247 | B2 | 2/2008 | Schmieding et al. |
| 7,846,170 | B2 | 12/2010 | Modesitt et al. |

(Continued)

FOREIGN PATENT DOCUMENTS

| CA | 1312518 | 1/1993 |
| CN | 102164548 A | 8/2011 |

(Continued)

OTHER PUBLICATIONS

International Search Report and Written Opinion of co-pendmg PCT Application No. PCT/US2019/021772 filed Mar. 12, 2019.

(Continued)

*Primary Examiner* — Melanie R Tyson
(74) *Attorney, Agent, or Firm* — Chambliss, Bahner & Stophel, P.C.; Stephen D. Adams

(57) ABSTRACT

In a method for providing a double loop stitch, a needle assembly having a first needle portion and a second needle portion that is removably connected to the first needle portion is provided. Opposing ends of a thread are connected to the needle portions, forming a loop that is placed around a sewing material. The needle assembly is inserted through the sewing material at an insertion point. The thread is then partially pulled through the sewing material at the insertion point such that a pair of loops of thread, separated by the insertion point, remain adjacent a first face of the sewing material. The needle portions are then separated and are passed around opposite sides of the sewing material from adjacent a second face back adjacent the first face. Each needle portion is then passed through one of the loops. The loops are then cinched and locked in place.

18 Claims, 15 Drawing Sheets

(56) References Cited

U.S. PATENT DOCUMENTS

| | | |
|---|---|---|
| 8,298,284 B2 | 10/2012 | Cassani |
| 8,388,653 B2 | 3/2013 | Nobis et al. |
| 8,591,544 B2 | 11/2013 | Jolly et al. |
| 9,480,565 B2 | 11/2016 | Medema et al. |
| 9,545,251 B2 | 1/2017 | Bojarski et al. |
| 9,622,742 B2 | 4/2017 | Spenciner |
| 9,993,241 B2 | 6/2018 | Denham et al. |
| 9,993,332 B2 | 6/2018 | Woodruff et al. |
| 2007/0060788 A1 | 3/2007 | Gellman |
| 2007/0173887 A1 | 7/2007 | Sasaki |
| 2008/0051833 A1 | 2/2008 | Gramuglia et al. |
| 2009/0105752 A1 | 4/2009 | Shonteff et al. |
| 2011/0213387 A1 | 9/2011 | Nguyen et al. |
| 2011/0264138 A1 | 10/2011 | Avelar et al. |
| 2012/0046746 A1 | 2/2012 | Konicek |
| 2013/0289597 A1 | 10/2013 | Guo |
| 2016/0175088 A1 | 6/2016 | Sengun |
| 2016/0206307 A1 | 7/2016 | Wack et al. |
| 2017/0172725 A1 | 6/2017 | Gustafson |
| 2017/0303956 A1 | 10/2017 | Misle et al. |
| 2018/0014926 A1 | 1/2018 | Cassani |
| 2018/0185022 A1 | 7/2018 | Mohamed et al. |
| 2018/0193015 A1 | 7/2018 | Denham et al. |
| 2018/0221133 A1 | 8/2018 | Lund |
| 2018/0271640 A1 | 9/2018 | Woodruff et al. |

FOREIGN PATENT DOCUMENTS

| | | |
|---|---|---|
| CN | 204600572 U | 9/2015 |
| CN | 107582182 A | 1/2018 |
| DE | 69820014 T2 | 9/2004 |
| DE | 102008044855 A1 | 3/2010 |
| DE | 20217001689 U1 | 6/2017 |
| EP | 0415915 B1 | 10/1996 |
| EP | 2359754 A2 | 8/2011 |
| ES | 1060450 | 9/2005 |
| JP | 2007-283061 | 11/2007 |
| KR | 10-1611732 | 4/2016 |
| WO | WO 2010/103467 A1 | 9/2010 |
| WO | WO 2015/072797 A1 | 5/2015 |
| WO | WO 2018/009637 A1 | 1/2018 |

OTHER PUBLICATIONS

White et al., "Krackow Locking Stitch Versus Locking Premanufactured Loop Stitch for Soft-Tissue Fixation," Arthroscopy, 26(12):1662-1666, Dec. 2010.

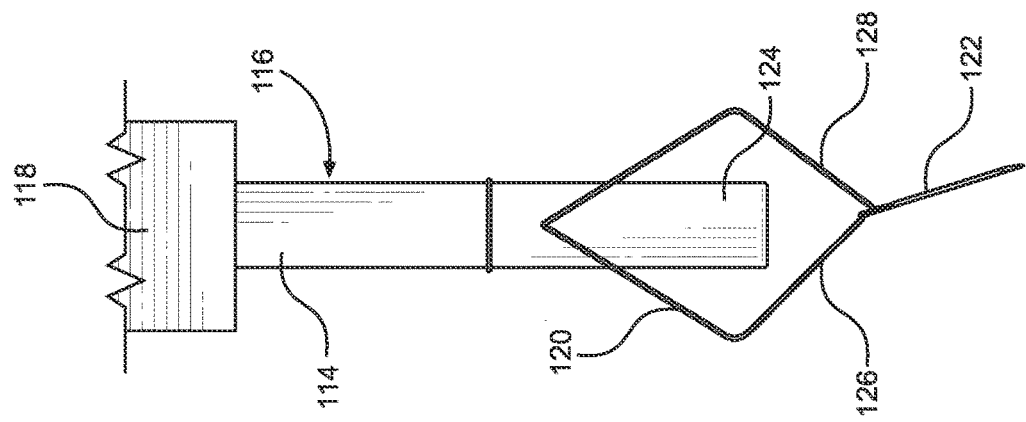
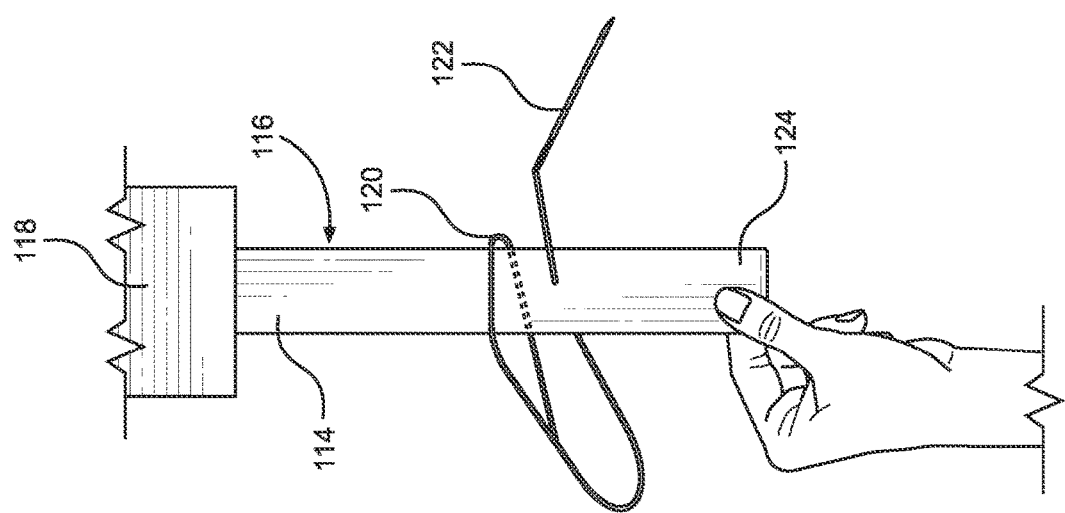
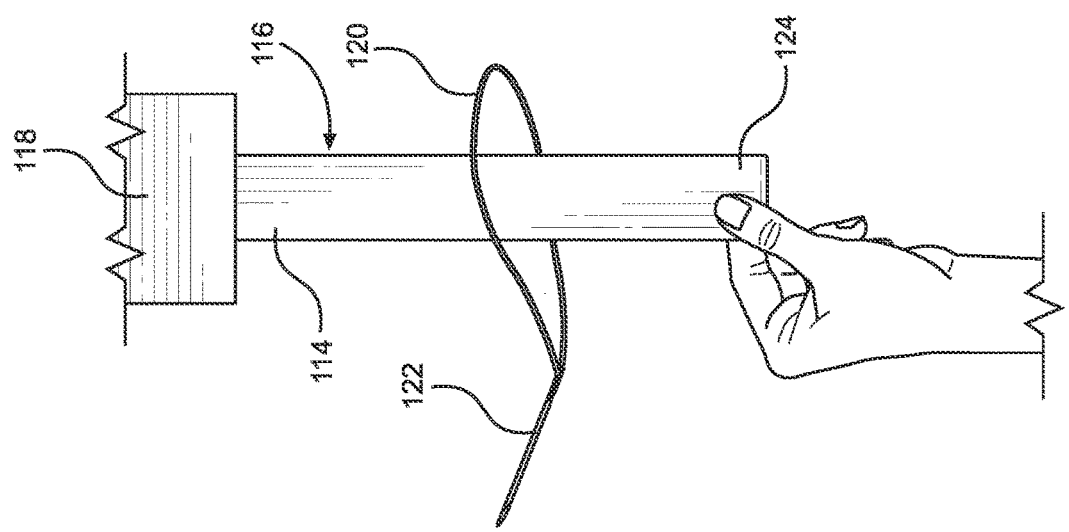

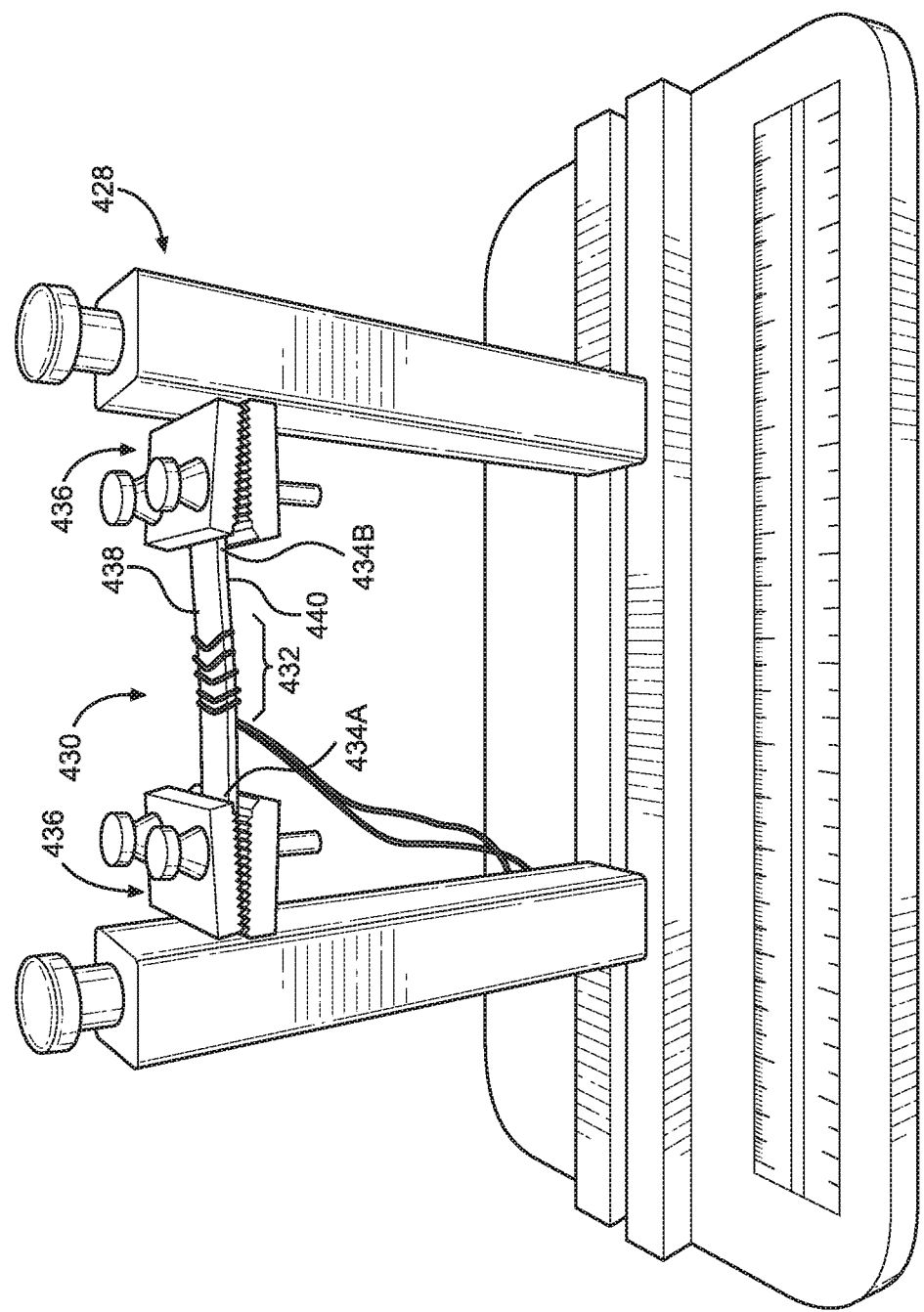

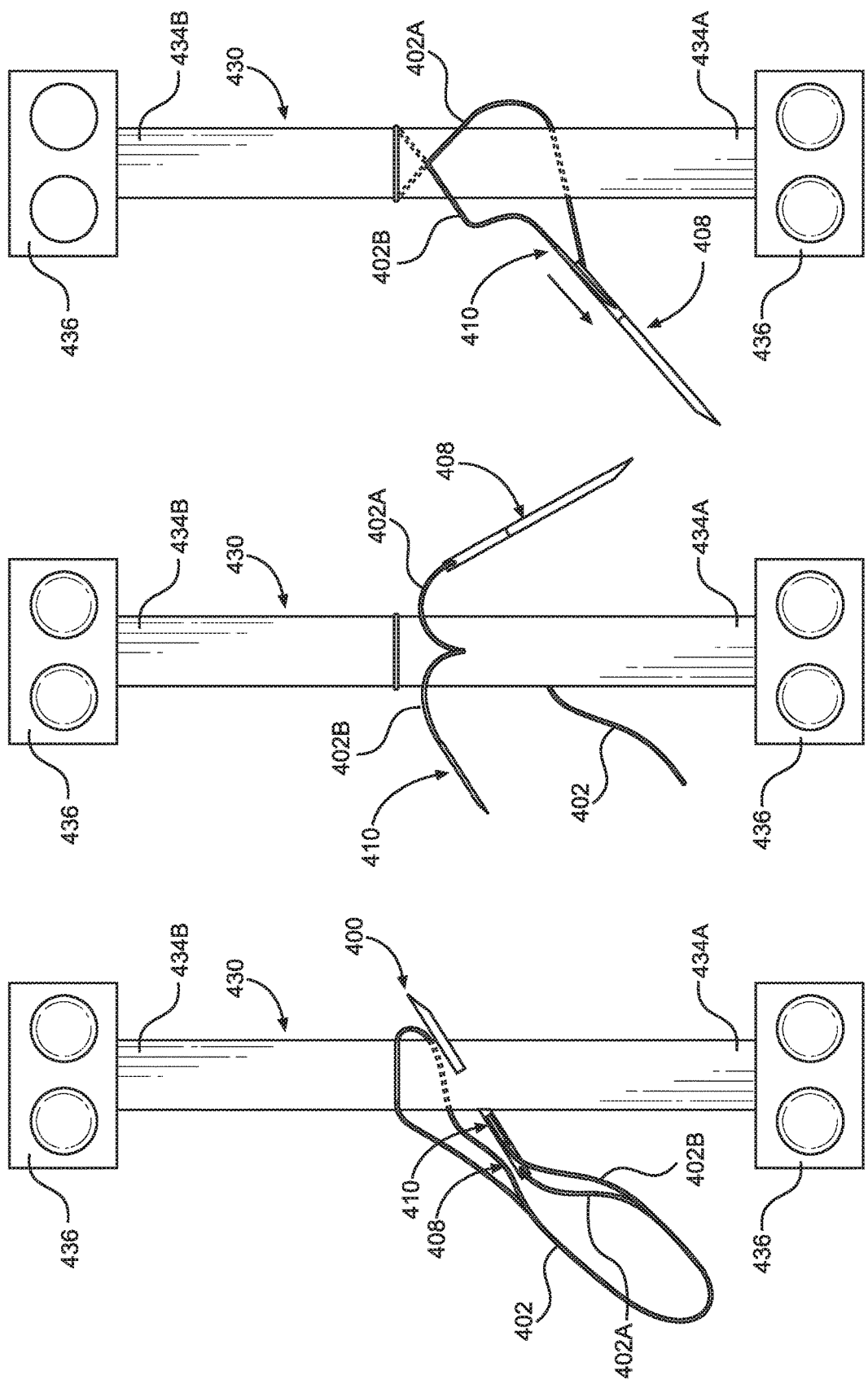

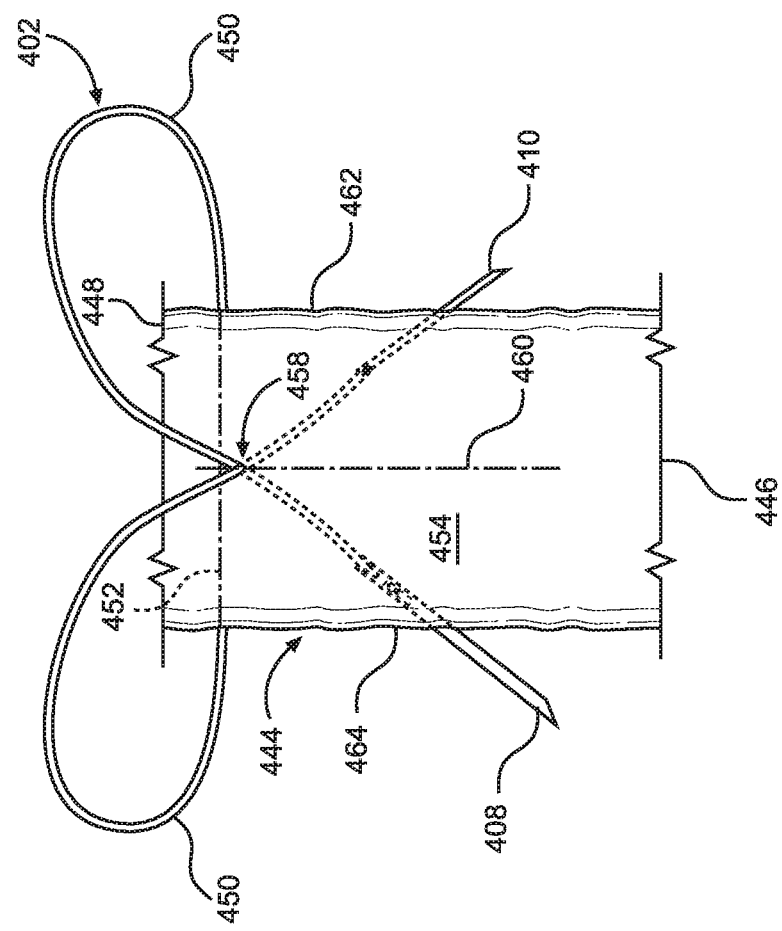
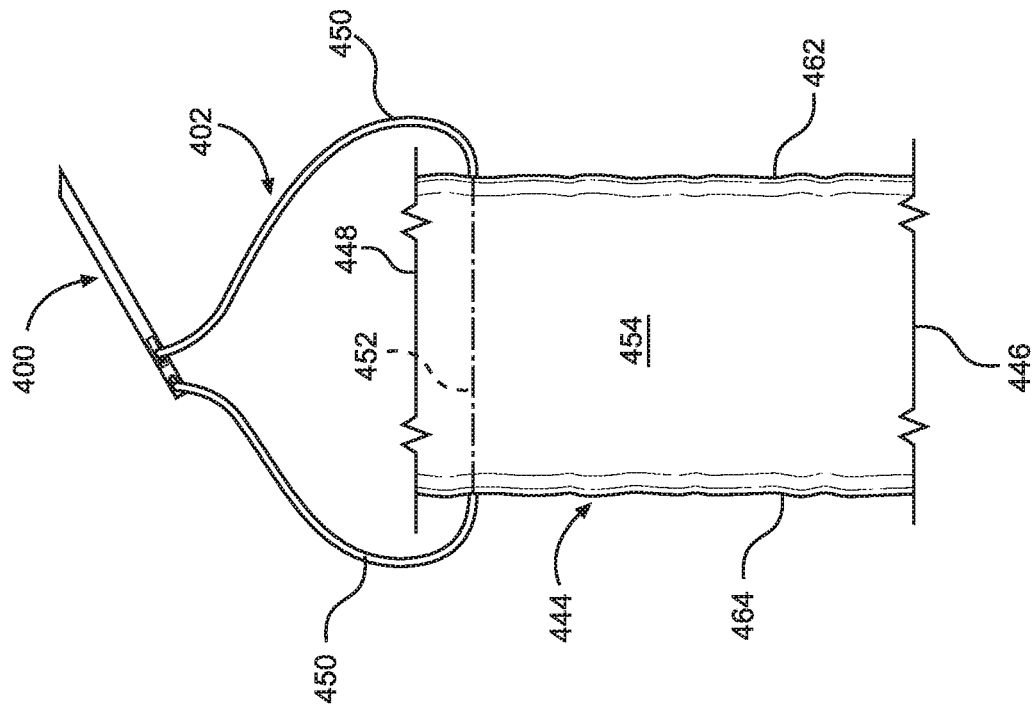

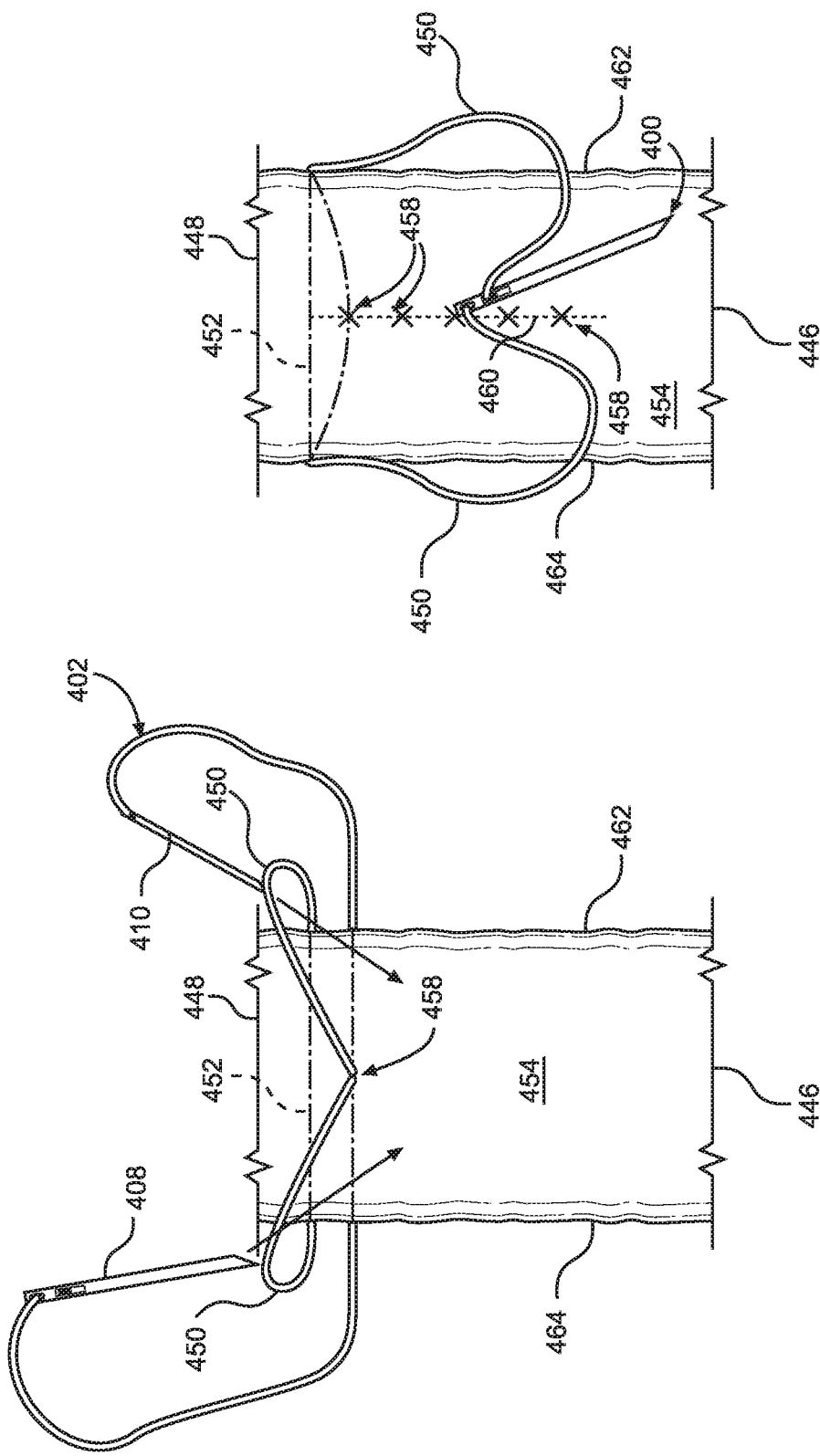

METHODS AND SYSTEMS FOR DOUBLE LOOP STITCHING

CROSS-REFERENCE TO RELATED APPLICATIONS

This application is a continuation-in-part of application Ser. No. 16/151,591, filed Oct. 4, 2018, which claims priority to U.S. Provisional Patent Application No. 62/586,690, filed on Nov. 15, 2017, both entitled METHODS AND SYSTEMS FOR DOUBLE LOOP STITCHING, the entire contents of both applications being incorporated herein by reference.

FIELD OF THE INVENTION

This invention generally relates to a method and apparatus for stitching. More specifically, the present invention, relates to an improved method and apparatus for reinforcing sewing materials using stitches, including in orthopedic reconstruction procedures using a soft tissue grafts that are reinforced with stitches.

BACKGROUND OF THE INVENTION

Ligament replacement or repair is very common amongst athletes and active individuals. Two examples of ligaments that are commonly injured and require replacement or repair are the anterior cruciate ligament (ACL) and the posterior cruciate ligament (PCL). The ACL and the PCL are bands of fibrous tissue that are located at the knee joint and that connect the tibia to the femur. These ligaments assist in controlling the flexion and extension of the leg, and sprains and tears, particularly to the ACL, are among the most common sports-related injuries. Injuries to the ACL often occur when the athlete turns or moves suddenly when running or jumping. Depending on the nature and severity of the injury, treating a torn or strained ACL or PCL may or may not require surgery. Non-surgical methods include bracing and physical therapy. On the other hand, when the damage is more severe, a torn ACL or PCL may be stitched back together using sutures. In even more severe cases, where the ligament cannot be stitched, it is typically replaced entirely.

With initial reference to FIGS. 1 and 2, knee 100 is depicted after undergoing an ACL replacement procedure. In a typical ACL replacement surgery, the torn ligament is replaced by soft tissue graft 102, which may be taken from the patient's own body or from a donor. The graft is commonly taken from the knee, hamstring, or quadriceps. The surgeon then uses a needle and heavy-duty, non-degradable suture to reinforce the ends of the graft. The graft is then implanted into the knee and affixed so that it serves the same anatomical function that the torn ACL served prior to tearing. More particularly, the graft provides a support structure that enables a new ligament to grow. During the procedure, the first step is to remove the torn ligament. Next, the graft is prepared for insertion into the knee. Among other things, this preparation may include folding the replacement tendon onto itself to form layered strands of tissue (FIG. 2) and then stitching the strands together to create graft 102 with one or more stitched sections 104 that have adequate strength and the correct length. Once graft 102 has been prepared, holes or "tunnels" 106 are drilled into tibia 108 and femur 110. Ends 112 of graft 102 are then inserted into tunnels 106 and are fixed in place. The above-described process for graft preparation is known in the art and is discussed, for example, in U.S. Pat. No. 8,298,284, entitled "Whip Stitched Graft Construct and Method of Making the Same" (hereinafter, "Arthrex").

A conventional graft preparation process, such as that described in Arthrex, is illustrated in FIGS. 3A-3E. According to the illustrated method, one end (such as distal portion 114) of a graft 116 is securely held by stationary work station 118. A continuous or closed loop of suture material 120 having needle 122 is placed around graft 116 such that the graft passes through the loop. Proximal portion 124 of graft 116 is held by hand or by a tool in a user's hand. Proximal portion 124 of graft 116 is not connected to work station 118; rather, the proximal portion is typically grasped by hemostats, forceps, etc. Next, needle 122 is inserted through a first side of graft 116 (e.g., bottom of the graft) and the needle and suture 120 are pulled through to the second side of the graft e.g., the top of the graft). From there, the process of passing needle 122 through the first side of graft 116 and then pulling the needle and suture 120 through to the second side of the graft is repeated multiple times until the desired number of stitches have been created. Ideally, needle 122 enters the same side of graft 116 for each stitch. To move needle 122 back to the bottom of the graft 116 in preparation for each subsequent stitch, proximal portion 124 of graft 116 is passed through the loop of suture material 120. Put differently, the loop of suture material 120 passes around proximal portion 124 of graft 116. This step typically requires the user to release their grip on proximal portion 124 of graft 116 so that the proximal portion can pass through the loop. Passing the loop of suture material 120 around proximal portion 124 of graft 116 requires spreading the loop to form first loop portion 126 and second loop portion 128. When needle 122 is brought back below graft 116, first loop portion 126 passes over the left-most edge of graft and second loop portion 128 of the suture material passes over the right-most edge of the graft. Loop portions 126, 128 come back together below graft 116. From there, needle 122 and suture material 120 are inserted through graft 116 repeatedly to create a pattern of stitches, often called a "whip stitch" pattern, which extends along at least a portion of graft.

One problem with the conventional graft preparation process discussed above is that only distal portion 114 of graft 116 is fixed and stationary when creating the whip stitch pattern. This enables non-fixed proximal portion 124 of the graft 116 to move during the stitching process. Movement of graft 116 during the stitching process can result in non-uniform stitch positioning and spacing, which can ultimately lead to failure of the graft, such that a revision (i.e., follow-up) surgical procedure is required.

Another conventional graft preparation process utilizing the "Krackow" method of stitching is illustrated in FIGS. 12 and 13. The Krackow stitch is a running, locking stitch that is often used in soft-tissue fixation, such as in ACL reconstruction, Achilles tendon, medial collateral ligament, and patellar or quadriceps tendon repair. The repair may be made using graft 130 that has first side 132, second side 134, proximal portion 136 (i.e., the tip of the graft) and distal portion 138. Single suture 140 (typically attached to single curved needle 142) creates looping stitches along first side 132 (located on one side of centerline 144), which progress away from proximal portion 136 and towards distal portion 138. Before forming a new stitch (e.g., Stitch B), needle 142 is looped around suture 140 at the point where the previous stitch (e.g., Stitch A) was formed to create a locking pattern. After the stitches on first side 132 of graft 130 (i.e., Stitches A-C) are complete, needle 142 is passed across graft 130 to second side 134 (located on a second side of centerline 144) and stitches are formed in a similar fashion along the second side (i.e., Stitches D-F). The second set of stitches progress away from distal portion 138 and towards proximal portion 136. Again, before forming a new stitch (e.g., Stitch E), needle 142 is looped around suture 140 at the point where the previous stitch (e.g., Stitch D) was formed to create a locking pattern.

One problem with the conventional graft preparation process discussed above is that the process is slow because stitches must be formed along each side 132, 134 of graft 130 separately. Needle 142 must be inserted through graft 130 each time a stitch is made, which is time consuming and, due to the large number of punctures, could possibly weaken the strength of the graft. Additionally, since one set of stitches progresses away from proximal portion 136 and the other progresses away from distal portion 138, first side 132 and second side 134 of graft 130 may exhibit different holding or tear-out characteristics.

What is needed, therefore, is a method and apparatus for creating a double-loop stitch in a graft that is stronger, faster and that yields better and more consistent results than the conventional methods discussed above.

Notes on Construction

The use of the terms "a", "an", "the" and similar terms in the context of describing the invention are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value which the term modifies, but rather to provide an approximation of the value of such physical or functional characteristic.

Terms concerning attachments, coupling and the like, such as "attached", "connected" and "interconnected", refer to a relationship wherein structures are secured or attached to one another either directly or indirectly through intervening structures, as well as both moveable and rigid attachments or relationships, unless specified herein or clearly indicated by context. The term "operatively connected" is such an attachment, coupling or connection that allows the pertinent structures to operate as intended by virtue of that relationship.

The use of any and all examples or exemplary language (e.g., "such as" and "preferably") herein is intended merely to better illuminate the invention and the preferred embodiments thereof, and not to place a limitation on the scope of the invention. Nothing in the specification should be construed as indicating any element as essential to the practice of the invention unless so stated with specificity.

The apparatus and method disclosed herein may be used for traditional sewing processes, such as joining fabric or textiles in the production of clothing, etc., in surgical procedures, and other similar processes. As such, in the description that follows, the term "thread" is used broadly and interchangeably to refer to textile-type strands used in traditional sewing processes, to refer to medical sutures or other similar materials for use in performing surgery, and the like. Similarly, the term "sewing" is used broadly to refer to the traditional sewing type processes or surgical procedures that use needle and thread. Lastly, the term "sewing material" is used broadly to refer to textile or other types of materials used in traditional sewing type processes or to graft and other similar materials used in surgical procedures, such as ligaments, tendons, or other soft tissue.

SUMMARY OF THE INVENTION

The above and other needs are met by a sewing needle for passing a thread through a sewing material. The needle includes a needle tip configured to initially pass through said sewing material and a trailing end located at an opposite end of the needle from the needle tip. Preferably, the needle tip is integrally formed at an end of the first needle portion. A first needle portion follows the needle tip through said sewing material and a second needle portion is removably connected to the first needle portion and follows the needle tip through said sewing material. The needle also includes a first thread connection located on the first needle portion that is configured to carry a first portion of said thread through the sewing material and a second thread connection located on the second needle portion that is configured to carry a second portion of said thread through the sewing material.

Also disclosed herein is a method for providing a double loop stitch. First, a needle assembly formed from a first needle portion and a second needle portion that is removably connected to the first needle portion is provided. A first thread connection is located on the first needle portion and a second thread connection is located on the second needle portion. A thread having a first end connected to the first needle portion via the first thread connection and a second end connected to the second needle portion via the second thread connection and a loop formed between the first end and the second end is provided. Lastly, a sewing material having a proximal portion, a distal portion, a first face, a second face opposing the first face, a first side edge, and a second side edge opposite the first side edge is provided. A stitch is created in the sewing material with the needle assembly and thread. In creating the stitch, the needle assembly is inserted through the sewing material in a first direction at a first insertion point. The needle assembly enters the first face and exits the second face and the first and second ends of the thread are carried through the first insertion point by the first and second needle portions, respectively. The thread is partially pulled through the first insertion point such that a portion of the loop remains adjacent the first face of the sewing material. The first needle portion is disconnected and separated from the second needle portion, thereby also separating the first and second ends of the thread. The first needle portion and the first end of the thread are passed around the first side edge of the sewing material and then through the portion of the loop adjacent the first face. Similarly, the second needle portion and the second end of the thread are passed around the second side edge of the sewing material and through the portion of the loop adjacent the first face.

BRIEF DESCRIPTION OF THE DRAWINGS

The presently preferred embodiments of the invention are illustrated in the accompanying drawings, in which like reference numerals represent like parts throughout, and in which:

FIGS. 3A-3E illustrate a conventional method for providing a double loop stitch where the material being sewn is fixed only at one end;

FIG. 10 depicts a graft preparation station including a graft fixed at both ends and having a portion provided with double loop stitches according to a method of the present invention;

FIGS. 11A-11E illustrate a process for providing a double loop stitch in a material that is fixed at both ends using a two-part needle assembly according to a method of the present invention;

FIGS. 16-19 illustrate a process for providing a hybrid bilateral locking loop stitch using a two-part needle assembly according to a method of the present invention.

DESCRIPTION OF THE PREFERRED EMBODIMENTS OF THE INVENTION

Figure 1:
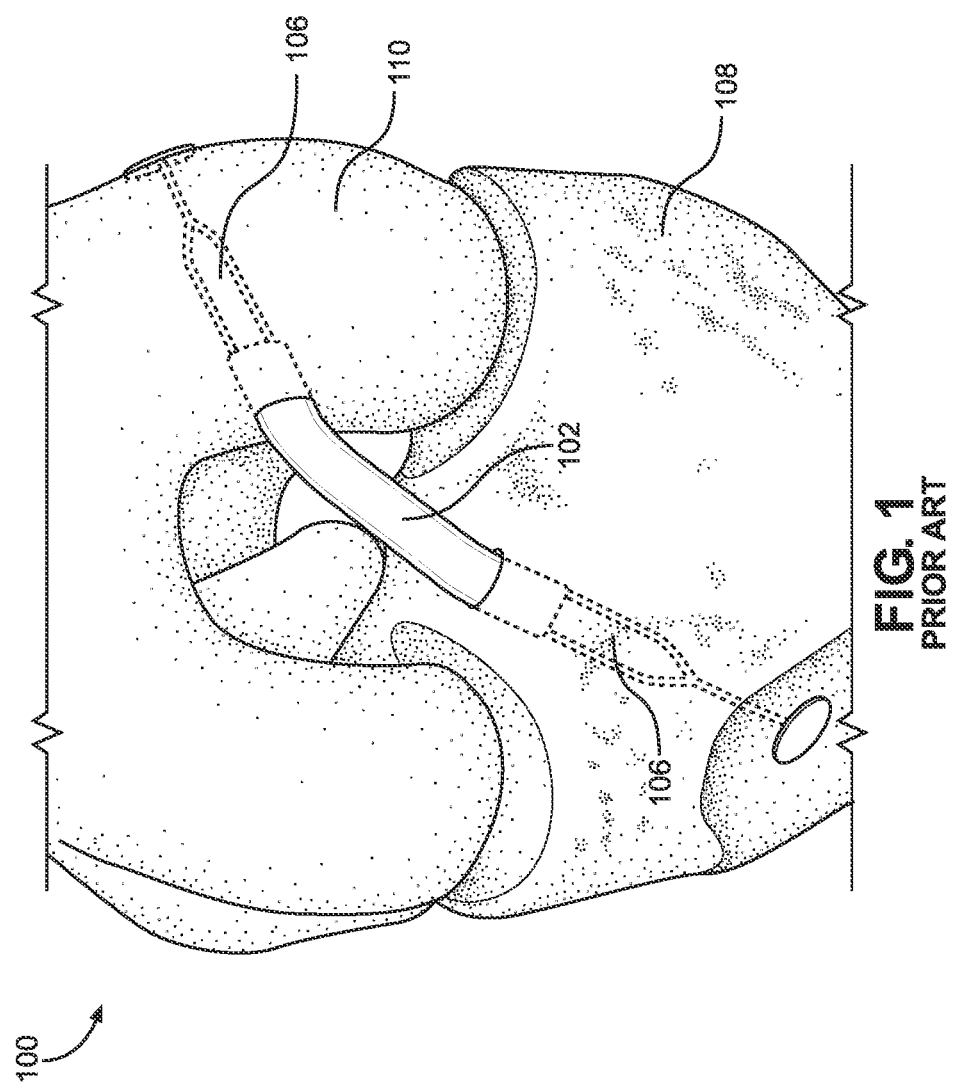
FIG. 1 depicts a knee following an ACL reconstruction procedure.
Figure 2:
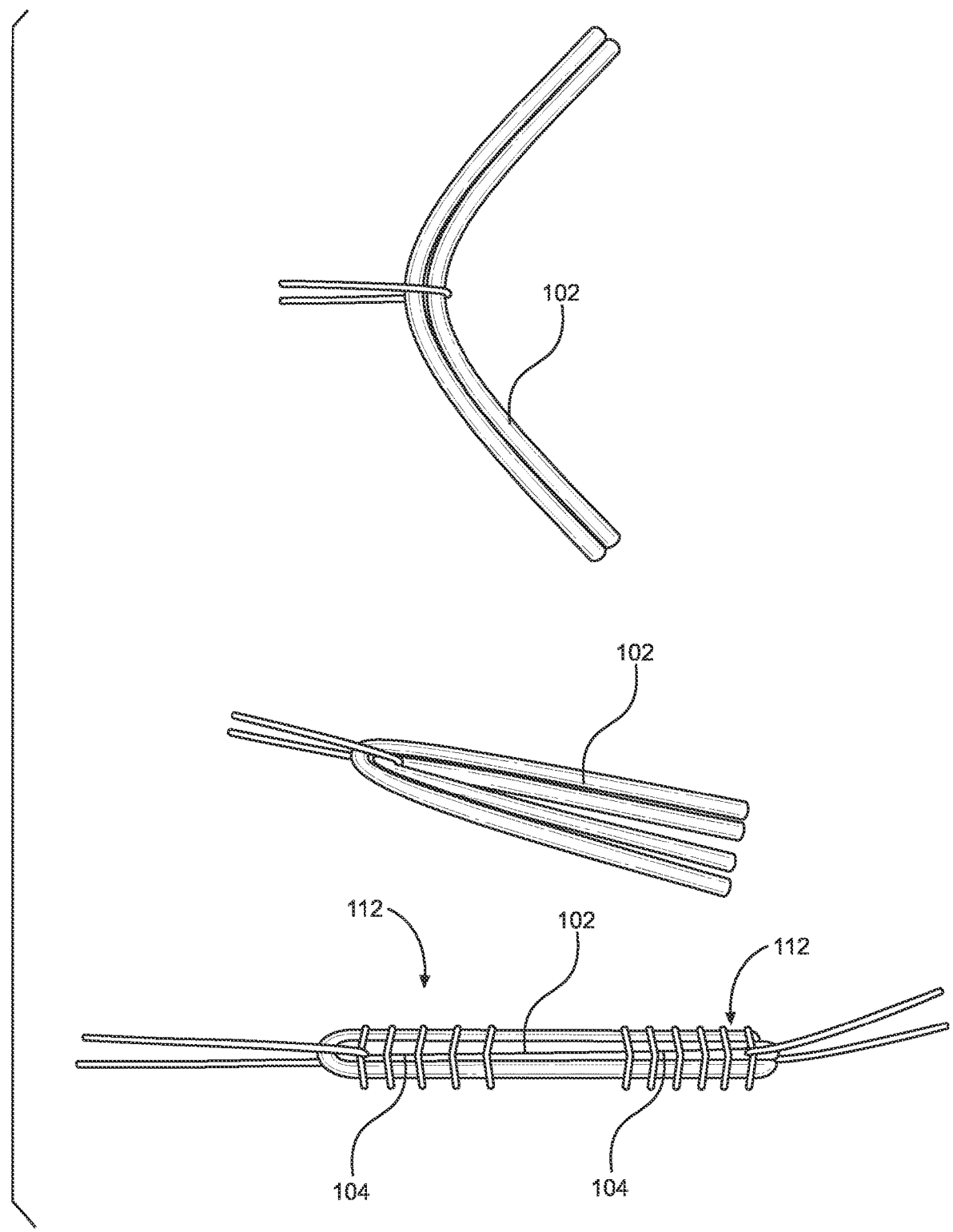
FIG. 2 provides side elevation views depicting a tendon being folded and sutured in preparation for an ACL reconstruction procedure.

This description of the preferred embodiments of the invention is intended to be read in connection with the accompanying drawings, which are to be considered part of the entire written description of this invention. The drawings are not necessarily to scale, and certain features of the invention may be shown exaggerated in scale or in somewhat schematic form in the interest of clarity and conciseness.

With reference now to FIGS. 4-9, there is provided two-part sewing needle assembly 400 for passing thread 402 through a sewing material. Assembly 400 includes needle tip 404 configured to initially pass through said sewing material. Trailing end 406 is located at an opposite end of assembly 400 from the needle tip 404 and is generally the last portion of assembly 400 to pass through the sewing material. Assembly 400 in this case is substantially linear along its length (i.e., along a line extending between the needle tip 404 and the trailing end 406). However, in other cases, at least a portion of the needle is curved along its length. Assembly 400 includes a first needle portion 408 that is configured to follow the needle tip 404 through the sewing material. In preferred embodiments, the needle tip 404 is integrally formed at an end of the first needle portion 408. Additionally, assembly 400 includes a second needle portion 410 that is configured to removably connect to the first needle portion 408 and to also follow the needle tip 404 through the sewing material. Depending on the respective dimensions (e.g., length) of the first and second needle portion 408, 410, the trailing end 406 of assembly 400 may be located on either the first needle portion or the second needle portion.

Continuous thread 402 is connected to both first and second needle portions 408, 410. First thread connection 412 is located on first needle portion 408 and is configured to carry first portion 402A of thread 402 through the sewing material. Likewise, second thread connection 414 is located on second needle portion 410 and is configured to carry second portion 402B of thread 402 through the sewing material. In the embodiment shown, single strand of thread 402 extends between first and second needle portions 408, 410, with one end of the thread strand being fixed at first thread connection 412 and the other end of the thread strand being fixed at second thread connection 414. However, thread 402 may form a continuous loop passing through both thread connections 412, 414, such that at least two strands of thread extend between first and second needle portions 408, 410. An advantage of the continuous loop is that needle portions 408, 410 may "float" along thread 402 and may be re-centered on the thread during the sewing process. Additionally, thread connections 412, 414 illustrated are openings (or eyes) that thread 402 is passed through. In other embodiments, thread connections 412, 414 are swaged (or eyeless) connections, where thread 402 is integrally formed with an end of needle portions 408, 410.

Assembly 400 and thread 402 may be used for traditional sewing tasks, such as in the manufacture or manipulation of textiles. In other embodiments, assembly 400 and thread 402 are used for surgical procedures and are made from surgical grade materials. When used for surgical procedures, an advantage of the swaged end design is reduced trauma to the tissue and patient.

First needle portion 408 and second needle portion 410 are configured to selectively and removably connect together, such that they pass substantially simultaneously through the sewing material. Receiver 416 is located on first needle portion 408 and is sized and configured to receive second needle portion 410 for removably connecting the first and second needle portions together. In this particular embodiment, receiver 416 is an elongate fully-enclosed canal that has been machined (e.g., bored) into and extends along at least a portion of the length of first needle portion 408. Receiver 416 has opening 424 at one end and stop 420 located at the opposite end. In this particular case, stop 420 is created by boring elongate receiver 416 only partially through first needle portion 408.

End 422 formed on second needle portion 410 is sized for sliding insertion into receiver 416 via opening 424. As second needle portion 410 slides into receiver 416, end 422 contacts stop 420 and the stop prevents the second needle portion from passing entirely through first needle portion 408. Advantageously, contacting end 422 with stop 420 provides tactile feedback to the user that provides assurance that second needle portion 410 has been fully inserted into and correctly located within first needle portion 408. Preferably, end 422 of the of second needle portion 410 is provided with a narrowed tip configured to initially engage opening 424 of receiver 416 for assisting in inserting and guiding the second needle portion into the receiver. For example, in certain embodiments, end 422 of second needle portion 410 comprises a second needle tip. However, in other embodiments, end 422 is blunted (i.e., not sharp) in order to help prevent inadvertent injury.

In certain embodiments, partially enclosed (i.e. concaved) post section 426 extending beyond opening 424 is formed on first needle portion 408. One purpose of post section 426 is to support and protect the portion of second needle portion 410 that extends beyond opening 424. The concaved sides of post section 426 extend partially around second needle portion 410 and help protect the second needle portion from damage (e.g., bending) while still allowing the second needle portion to be easily accessed. Post section 426 also provides a location for first thread connection 412, which is formed near the end of post section. Preferably, post section 426 is sized such that first thread connection 412 is fully exposed when second needle portion 410 is fully inserted into receiver 416 of first needle portion 408. Likewise, second thread connection 414 is also preferably fully exposed when second needle portion 410 is fully inserted into receiver 416 of first needle portion 408.

The above-described two-part needle assembly 400 may be used in carrying out an improved method for creating a whip stitch, including particularly in preparing a graft in a medical procedure, such as an ACL reconstruction surgery. With reference now to FIG. 10, graft preparation station 428 with exemplary ACL graft 430 having whip stitched section 432 is shown. End 434A, 434B of graft 430 are securely held by graft clamps 436 of graft preparation station 428 such that a portion of the graft extends between the clamps and the graft is held stationary and under slight tension. Positioning graft 430 between clamps 436 makes top face 438 and bottom face 440 of the graft, where needle assembly 400 must pass during the sewing procedure, easily accessible.

Figure 11E:
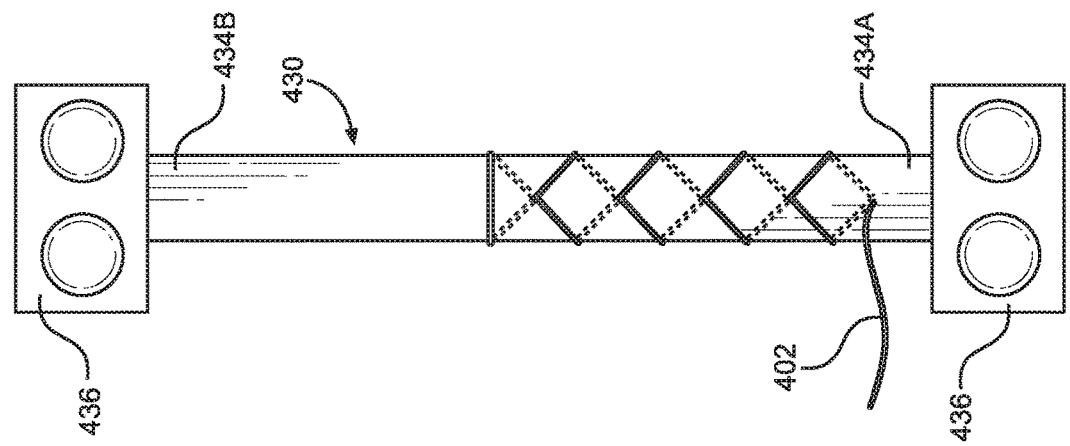

In FIGS. 11A-11E, a process of whip stitching tendon 430 (enlarged for clarity) using needle assembly 400 is illustrated. Referring initially to FIG. 11A, to begin the stitching process, graft 430 is placed into a graft station, as discussed above, such that ends 434A, 434B of the graft are securely held by graft clamps 436. Thread 402 is connected to needle assembly 400 such that first portion 402A of the thread is connected to first needle portion 408 and second portion 402B of the thread is connected to second needle portion 410. Needle assembly 400, arranged in a connected configuration such that first and second needle portions 408, 410 are connected together, is then inserted through graft 430 in a first direction such that the needle enters a first portion (e.g., bottom face 440) of the graft and exits a second portion (e.g., top face 438). By pulling needle assembly 400 through graft 430, both needle portions 408, 410 and both thread portions 402A, 402B are also carried through the graft.

Figure 11D:
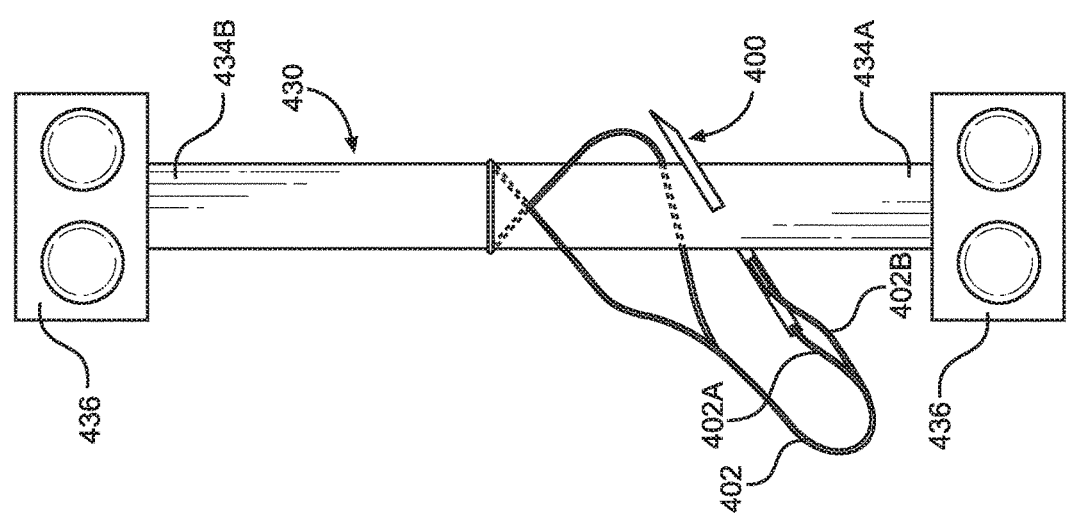
Figure 13:
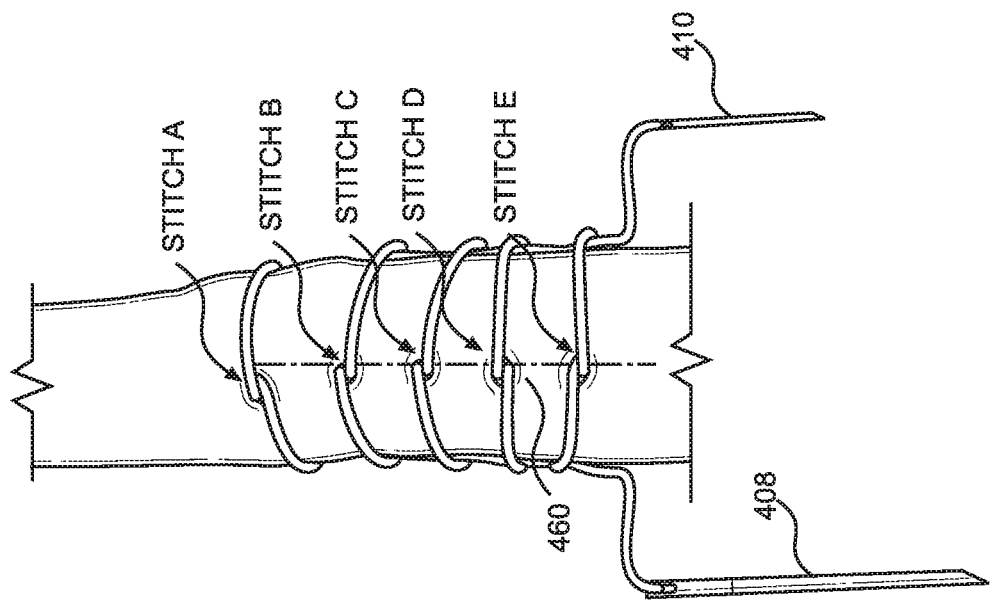
FIGS. 13-15 illustrate a graft that has been reinforced using a hybrid bilateral locking loop stitch using a two-part needle assembly according to a method of the present invention.
Figure 12:
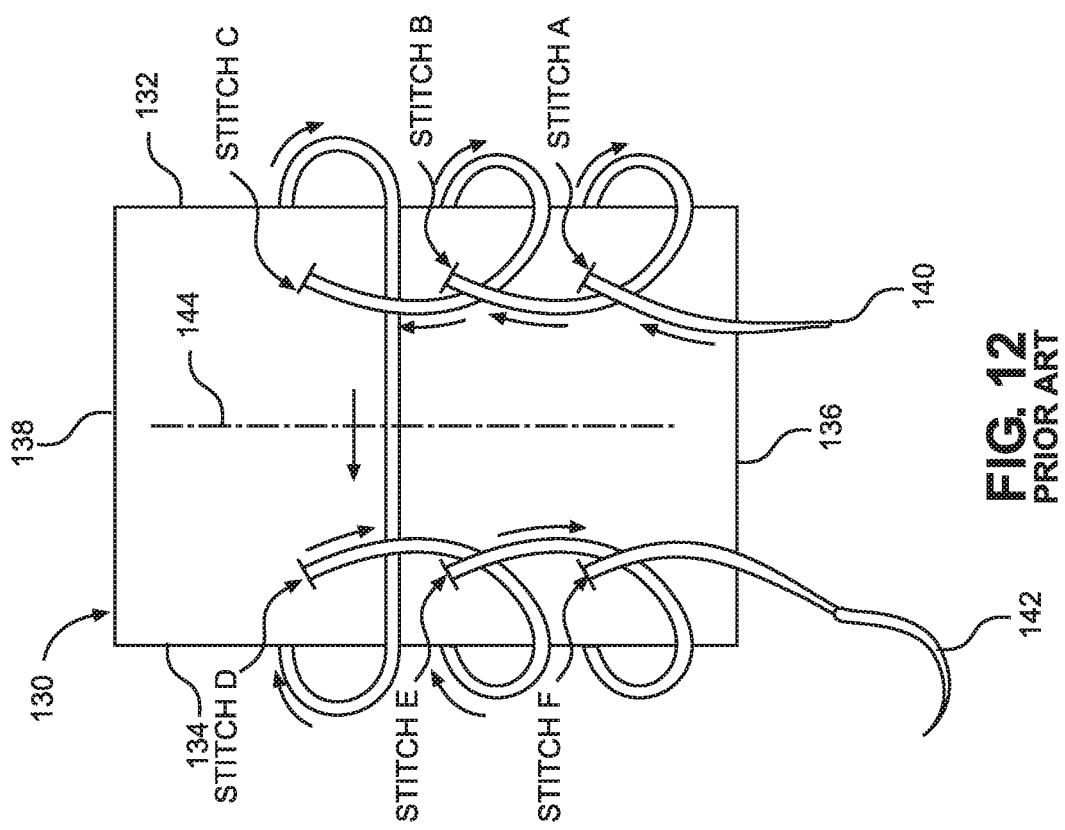
FIG. 12 illustrates a conventional method for forming a Krackow stitch.
Figure 14:
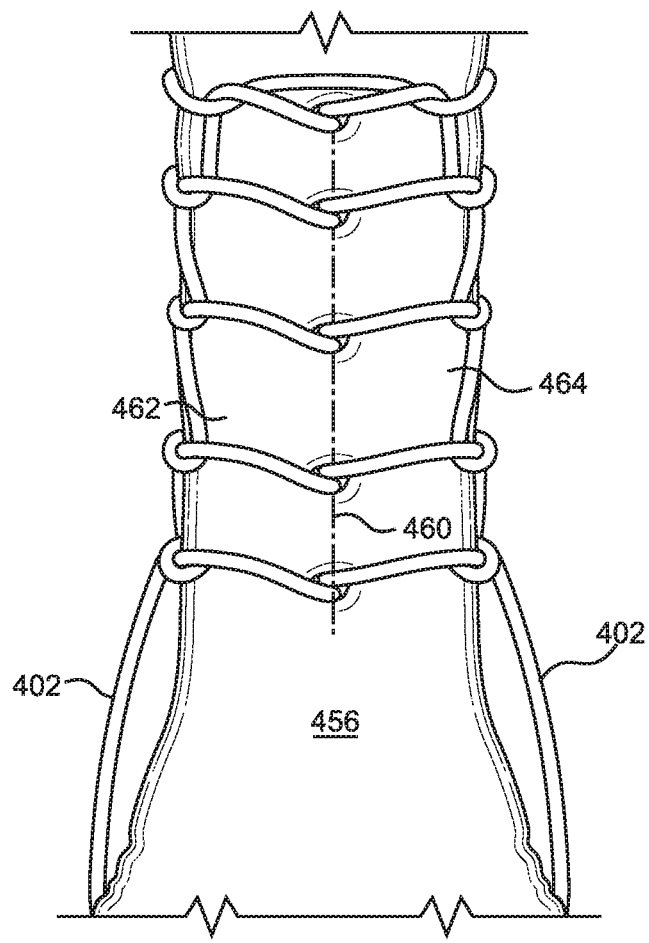
Figure 15:
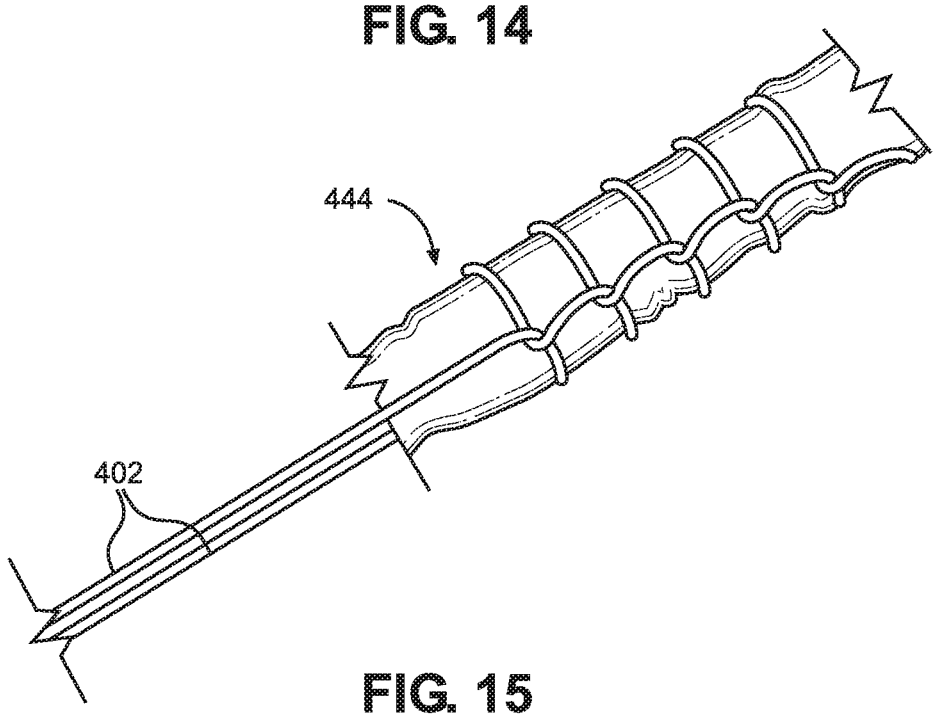

With reference to FIG. 11B, once needle assembly 400 has been pulled through graft 430, forming the first stitch, first needle portion 408 is separated from second needle portion 410, which also separates thread portions 402A, 402B. Once separated, thread portions 402A, 402B are brought around the outside of graft 430 back adjacent to the first portion (e.g., bottom face 440) in preparation for forming a second stitch. In the illustrated process, first thread portion 402A passes around the right edge of graft 430 and second thread portion 402B passes around the left of the graft. As shown in FIG. 11C, once thread portions 402A, 402B are moved back adjacent to the first portion (e.g., bottom face 440) of graft 430, first and second needle portions 408, 410 are reconnected. As shown in FIGS. 11D and 11E, once first and second needle portions 408, 410 are reconnected, needle assembly 400 is ready to form a second and subsequent stitches along the length of the graft by repeating the above-described process. After the required number of stitches are provided, graft 430 is removed from clamps 436. In the illustrated process, stitches are provided in only one end 434A of graft 430. However, using the same process, stitches may be provided at either or both ends 434A, 434B of graft 430.

Figure 3E:
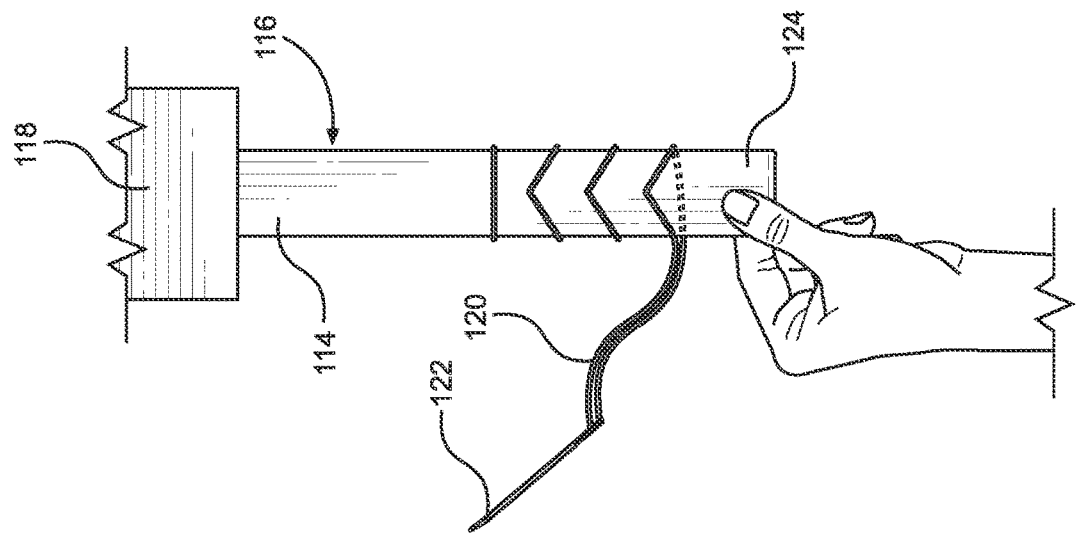
Figure 3D:
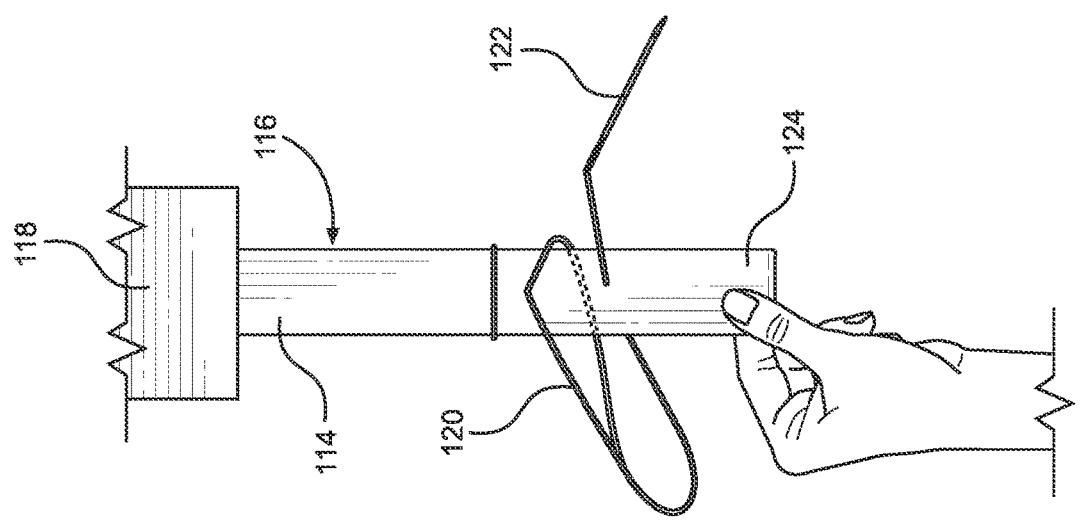
Figure 4:
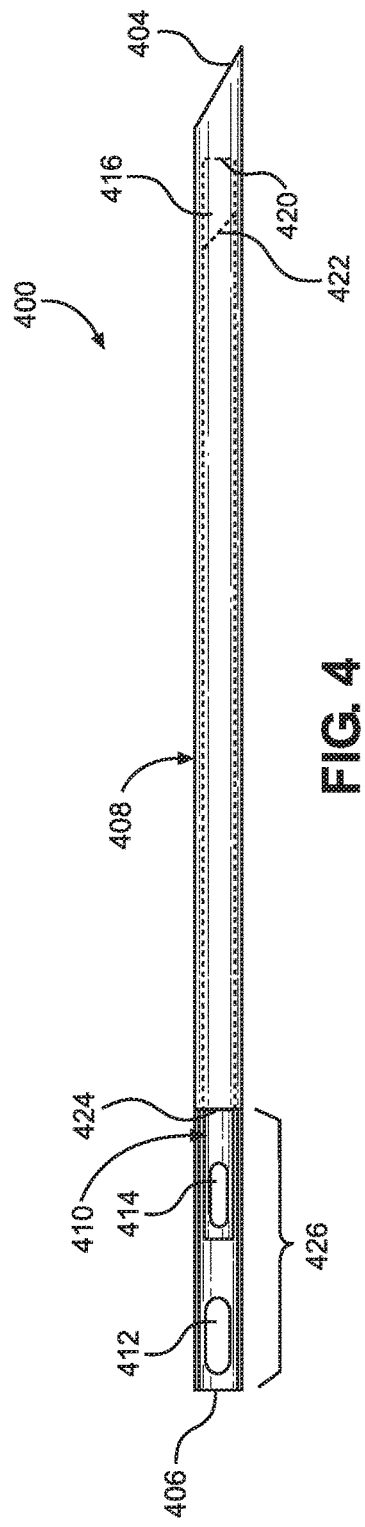
FIG. 4 is a sectional view depicting a needle assembly formed by a first needle portion and a second needle portion inserted into an elongate hollow receiver of the first needle portion according to an embodiment of the present invention.
Figure 5:
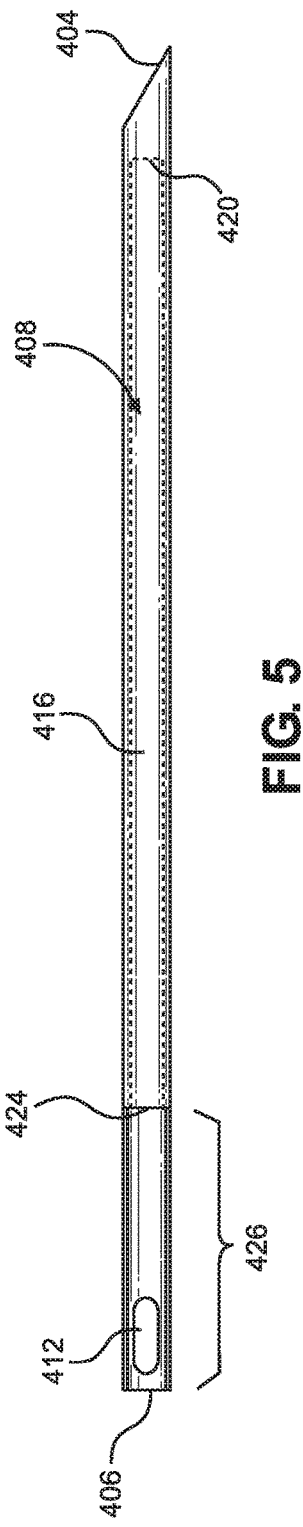
FIG. 5 is a sectional view depicting the first needle portion of FIG. 4.
Figure 6:
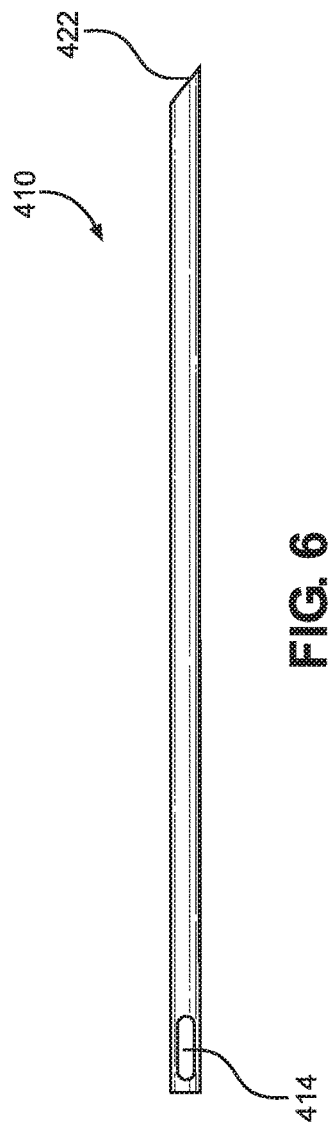
FIG. 6 is a sectional view depicting the second needle portion of FIG. 4.
Figure 7:
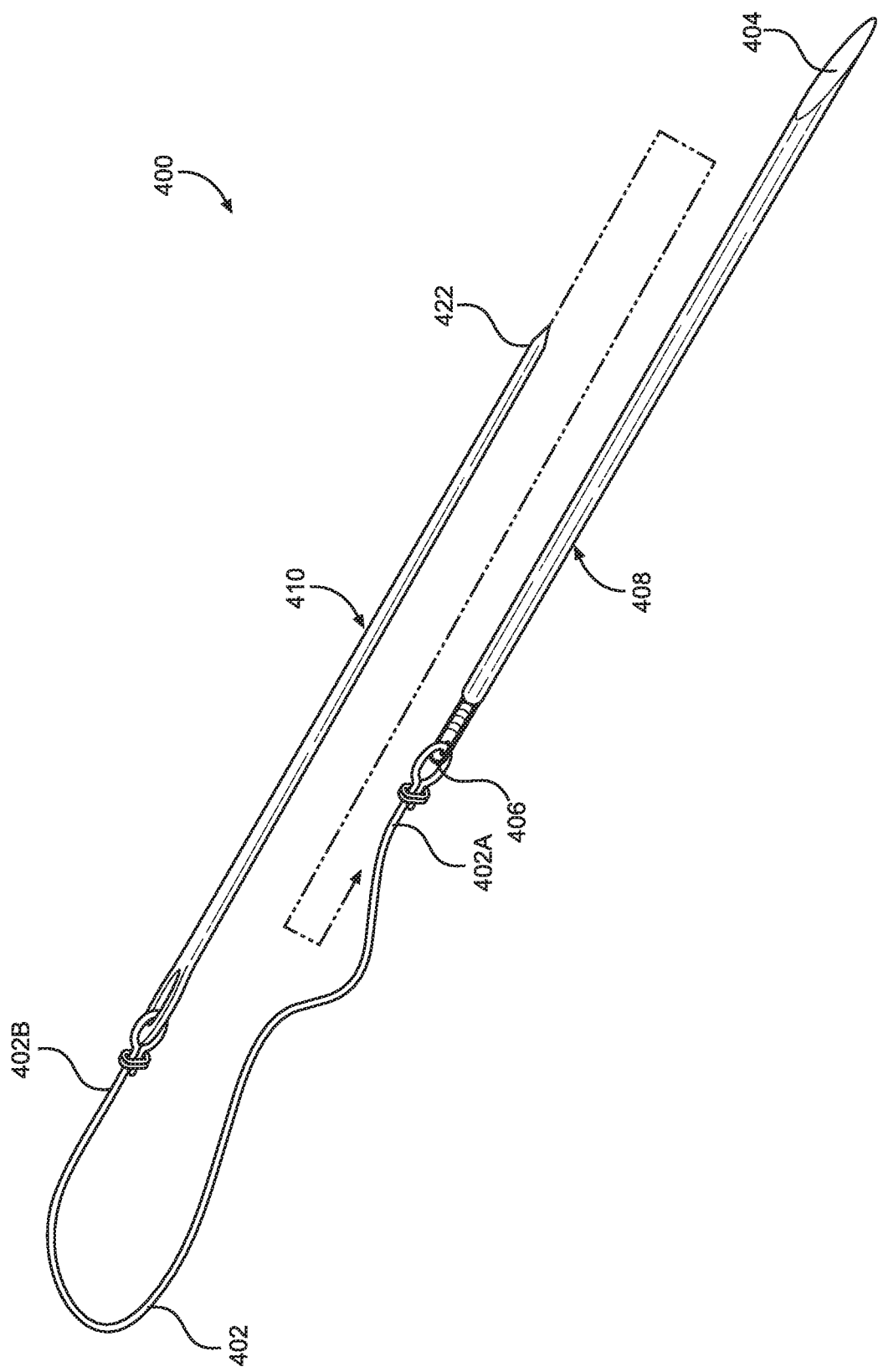
FIGS. 7 and 8 are perspective views depicting a thread connecting a first needle portion and second needle portion of a two-part needle assembly in a disconnected configuration.
Figure 8:
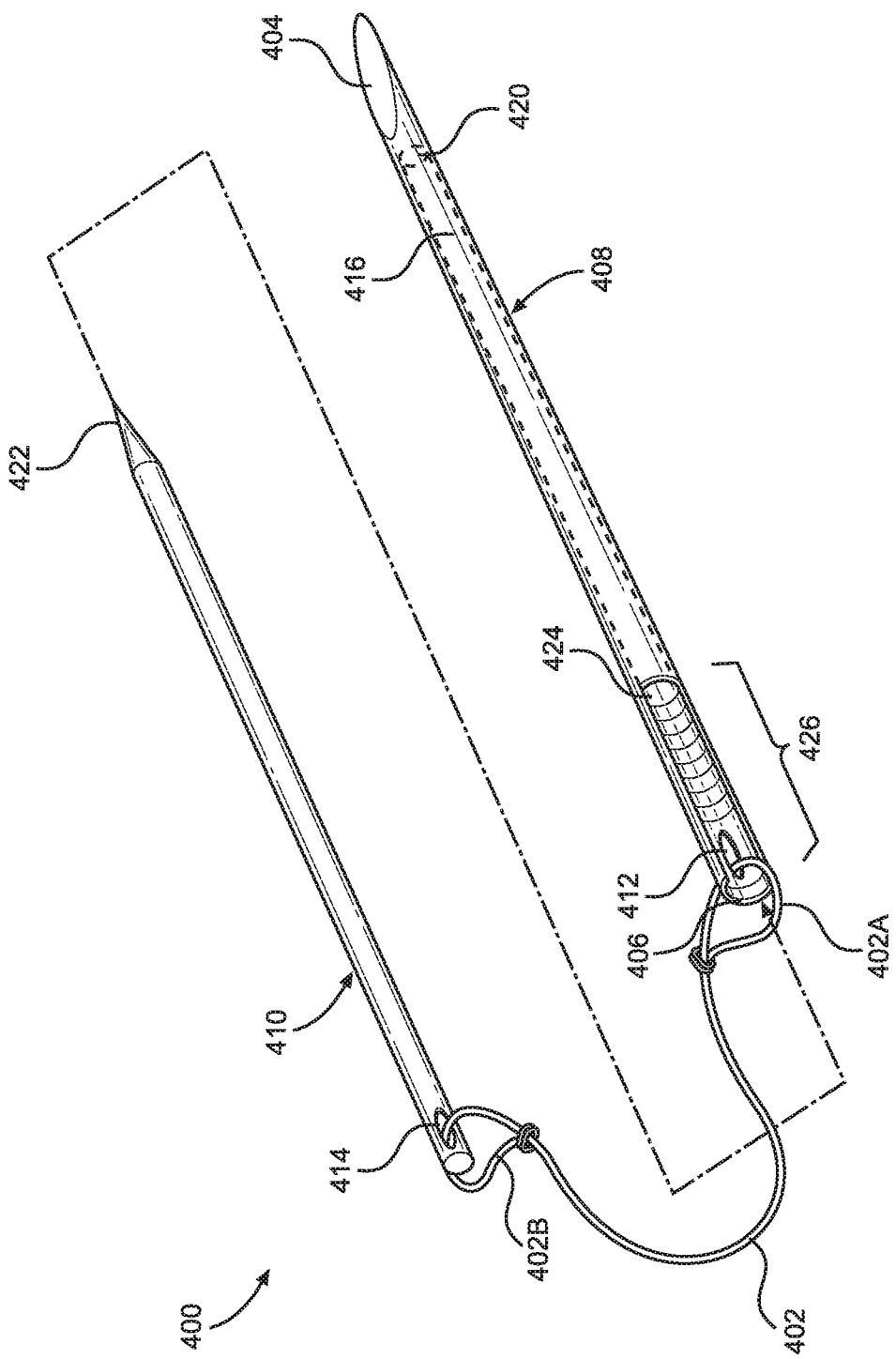
Figure 9:
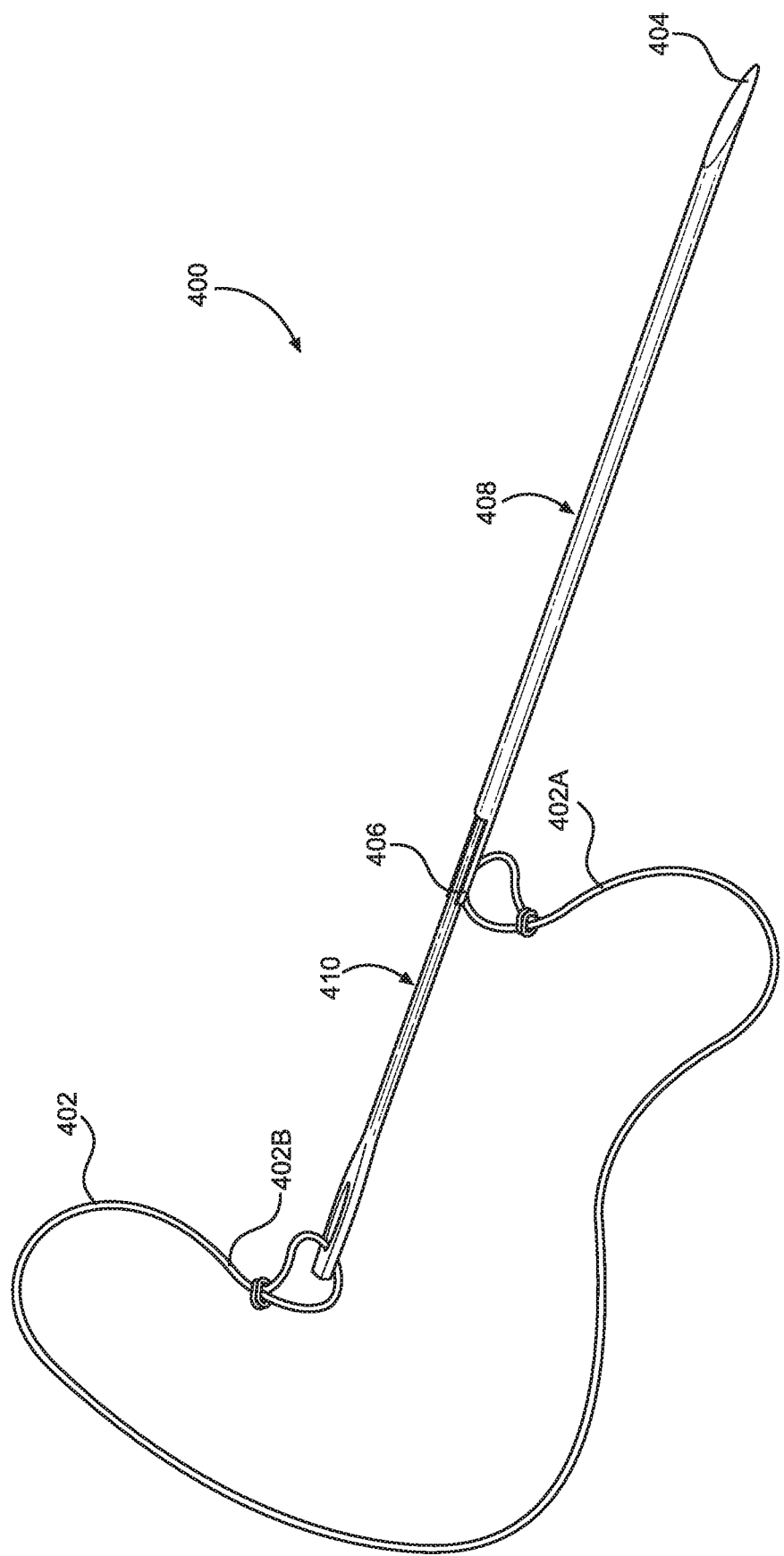
FIG. 9 depicts the second needle portion of FIGS. 7 and 8 partially inserted into the first needle portion.

As previously discussed, in conventional whip stitch methods, after forming a stitch the needle and thread are brought back to the first face of the graft by passing over a free end of the graft that is not fixed in a graft preparation station (see, e.g., Figure FIG. 3C). As such, that end of the graft freely moves during the preparation process, which may damage the graft and could result in inconsistent stitching. That inconsistency may impact the strength and quality of the graft and, ultimately, the failure rate of the surgery. In contrast, using the above-described two-part needle and stitching method, both ends of the graft remain fixed throughout the entire graft preparation process.

In FIGS. 13-19, a process of reinforcing sewing material 444 (such as a torn Achilles tendon) with a hybrid bilateral locking loop stitch (hereinafter, a "hybrid" stitch), which incorporates elements of a whip stitch and the Krackow stitch, using a two-part needle assembly 400 of the present invention, is illustrated. To begin the hybrid stitching process, proximal portion 446 and distal portion 448 of sewing material 444 may be placed into a graft station, as discussed above and are securely held by graft clamps (not shown). In other cases, the hybrid stitch is formed without being fixed in a graft station. For example, in the case of a torn Achilles tendon where only one end of the tendon has become detached from the patient's body, only the detached end of the tendon may be fixed using hemostats, Allis clamps, or the like.

Opposing ends of thread 402 are connected to first and second needle portions 408, 410 to form loop 450 of suture extending between the first and second needle portions. Once formed, loop 450 is preferably placed around first edge 462 and second edge 464 of sewing material 444 so that a portion 452 of loop 450 is adjacent second face 456, which is opposite first face 454. With reference to FIG. 17, first and second needle portions 408, 410 are connected together, and are then inserted through sewing material 444 in a first direction at first insertion point 458 such that needle assembly 400 enters first face 454 of the graft and exits second face 456 (shown in FIG. 15). Preferably, first insertion point 458 is located along centerline 460 of sewing material 444.

As shown in FIG. 18, needle assembly 400, including needle portions 408, 410, is then pulled through graft 430 and thread 402 is pulled partially through the graft. By only partially pulling thread 402 through sewing material 444, two separate portions of loop 450 remain adjacent first face 454 of the sewing material. These remaining portions of loop 450 create separate loops that are separated by insertion point 458. The ends of thread 402 are pulled to further reduce the size of loops 450. First and second needle portions 408, 410 are then each passed around one of side edges 462, 464 of sewing material 444 and then through one of smaller loops 450 located on either side of insertion point 458.

Preferably, both needle portions 408, 410 are inserted through loops 450 in the same direction towards proximal portion 446 of sewing material 444 and away from distal portion 448. However, in other embodiments, at least one of needle portion 408, 410 may be inserted through loop 450 in a direction toward distal portion 448 of sewing material 444 and away from proximal portion 446. Preferably, both needle portion 408, 410 are inserted through loops 450 substantially simultaneously with one another. Once needle portion 408, 410 have been inserted through loops 450, thread 402 is pulled taut in order to cinch loops 450 against sewing material 444, as shown in FIG. 19, to complete and lock the stitch formed at the first (top most, seen in FIG. 19) insertion point 458. First and second needle portions 408, 410 are then connected together again to form needle assembly 400. The sewing process may then be repeated by passing needle assembly 400 through the next insertion point 458. Preferably, the sewing progresses along centerline 460 in a direction that is towards the proximal portion 446 and away from distal portion 448.

By following the above-described process, a graft may be quickly reinforced with a number of stitches located at insertion points spaced along centerline 460. Each stitch includes a pair of loops 450 that are formed simultaneously by thread 402 and where one loop is located on each side of insertion point 458 along first and second edges 462, 464 of sewing material 444. Loops 450 encircle and lock thread 402 in place. However, in contrast to the prior art, loops 450 are not located near insertion point 458; rather, the loops are located along edges 462, 464 of the sewing material whereas the insertion point for the stitch is located long the center line of the sewing material.

In summary, the presently-disclosed process enables a graft to be prepared using a hybrid bilateral locking loop stitch that incorporates elements of a whip stitch and the Krackow stitch using a two-part needle assembly. Using this method, thread is inserted simultaneously through loops formed adjacent each side of the sewing material using the two separate needle portions. The needle portions are then combined to form a single needle assembly that creates a single line of stitches through the graft material along the center of the graft material, thereby eliminating the need to create two separate stitch groups and also reducing the possibility that the stitches will tear out of the graft material.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations as would be appreciated by those having ordinary skill in the art to which the invention relates.

What is claimed is:

1. A method for providing a double loop stitch comprising:
   providing a needle assembly having a first needle portion and a second needle portion that is removably connected to the first needle portion;
   providing a thread having a first end connected to the first needle portion and a second end connected to the second needle portion and a loop formed between the first end and the second end;
   providing a sewing material;
   creating a stitch in the sewing material with the needle assembly and thread by:
      passing the needle assembly through the sewing material at a first insertion point, such that the needle assembly and the first and second ends of the thread are carried through the sewing material at the first insertion point;
      pulling the thread partially through the sewing material such that a portion of the loop is not pulled through the sewing material;
      disconnecting the first needle portion from the second needle portion and separating the first and second ends of the thread;
      passing the first needle portion and the first end of the thread through the portion of the loop that was not pulled through the sewing material; and
      passing the second needle portion and the second end of the thread through the portion of the loop that was not pulled through the sewing material.

2. The method of claim 1 further comprising the step of:
   prior to creating the stitch at the first insertion point, placing the loop around the sewing material such that the sewing material is encircled by the loop and the needle assembly, and
   wherein, after pulling the thread partially through the sewing material, two separate loops are formed by the portion of the loop that was not pulled through the sewing material.

3. The method of claim 2 further comprising the steps of:
   passing the first needle portion and the first end of the thread through one of the two separate loops; and
   passing the second needle portion and the second end of the thread through the second one of the two separate loops.

4. The method of claim 1 further comprising the step of:
   prior to creating the stitch at the first insertion point, separating the first needle portion from the second needle portion and passing the first needle portion only through the sewing material;
   connecting the first needle portion to the second needle portion to form the needle assembly, wherein, after pulling the thread partially through the sewing material, two separate loops are formed by the portion of the loop that was not pulled through the sewing material.

5. The method of claim 4 further comprising the steps of:
   passing the first needle portion and the first end of the thread through one of the two separate loops; and
   passing the second needle portion and the second end of the thread through the second one of the two separate loops.

6. The method of claim 4 wherein the first needle portion only is passed through the sewing material prior to creating the stitch at the first insertion point in a first direction and the needle assembly is passed through the sewing material at the first insertion point in a second direction.

7. The method of claim 6 wherein the first direction and the second direction are offset by approximately 90 degrees.

8. The method of claim 1 further comprising the steps of:
   after forming the stitch at the first insertion point, connecting the first needle portion to the second needle portion to form the needle assembly; and
   passing the needle assembly through the sewing material at a second insertion point, such that the needle assembly and the first and second ends of the thread are carried through the sewing material at the second insertion point.

9. The method of claim 8 further comprising forming a plurality of stitches in the sewing material at each of a plurality of insertion points.

10. The method of claim 9 wherein the sewing material comprises a proximal portion and a distal portion, and wherein the plurality of stitches are formed in a direction that progresses towards the proximal portion and away from the distal portion.

11. The method of claim 1 wherein the first needle portion and the first end of the thread and the second needle portion and the second end of the thread pass through the loop in the same direction.

12. The method of claim 1 wherein the sewing material comprises a proximal portion and a distal portion, and wherein the first needle portion and the first end of the thread and the second needle portion and the second end of the thread pass through the loop in a direction that is towards the proximal portion and away from the distal portion.

13. The method of claim 1 wherein the sewing material comprises a proximal portion and a distal portion, and wherein the first needle portion and the first end of the thread and the second needle portion and the second end of the thread pass through the loop in a direction that is towards the distal portion and away from the proximal portion.

14. The method of claim 1 wherein the first needle portion and the first end of the thread and the second needle portion and the second end of the thread pass through the loop substantially simultaneously with one another.

15. The method of claim 1 further comprising the steps of:
   providing a stationary support having spaced apart connecting locations; and
   where the sewing material comprises a proximal portion and a distal portion, connecting the proximal portion and the distal portion of the sewing material to the spaced apart connecting locations of the stationary support such that a portion of the sewing material between the proximal and distal portions of the sewing material extends between the spaced apart connecting locations of the stationary support; and
   removing the proximal portion and the distal portion of the sewing material from the spaced apart connecting locations of the stationary support.

16. The method of claim 1 further comprising the steps of:
   in a reattachment surgical procedure performed on a patient's body, wherein a distal portion of the sewing material has not been detached from the patient's body and a proximal portion of the sewing material has been detached from the patient's body;
   clamping the proximal portion of the sewing material while the stitch is created in the sewing material; and
   unclamping the proximal portion of the sewing material prior to re-attaching the sewing material to the patient's body.

17. The method of claim 1 further comprising creating a plurality of stitches at insertion points spaced along a centerline of the sewing material, wherein each stitch includes a pair of loops formed simultaneously by the thread and where one loop is located on each side of the insertion points.

18. The method of claim 1 further comprising the steps of:
   inserting the second needle portion into the first needle portion to removably connect the first and second needle portions together to form the needle assembly, wherein the needle assembly has a leading end that is sized and configured to enter the sewing material and an opposing trailing end sized and configured to exit the sewing material as the needle assembly passes through and then entirely out of the sewing material,
   forming an opening in the sewing material for the needle assembly to enter using a needle tip located on the first needle portion;
   passing the needle assembly entirely through the sewing material such that the trailing end exits the sewing material.

* * * * *